United States Patent
Kan

(10) Patent No.: US 10,092,231 B2
(45) Date of Patent: Oct. 9, 2018

(54) PUSH-TO-CHARGE MECHANISM FOR LANCING DEVICE

(71) Applicant: FACET TECHNOLOGIES, LLC, Atlanta, GA (US)

(72) Inventor: Gil Kan, Alpharetta, GA (US)

(73) Assignee: Facet Technologies, LLC, Atlanta, GA (US)

( * ) Notice: Subject to any disclaimer, the term of this patent is extended or adjusted under 35 U.S.C. 154(b) by 226 days.

(21) Appl. No.: 14/835,174

(22) Filed: Aug. 25, 2015

(65) Prior Publication Data

US 2015/0359474 A1    Dec. 17, 2015

Related U.S. Application Data

(63) Continuation of application No. 14/026,129, filed on Sep. 13, 2013, now Pat. No. 9,149,221.
(Continued)

(51) Int. Cl.
*A61B 5/151* (2006.01)
*A61B 5/15* (2006.01)

(52) U.S. Cl.
CPC .......... *A61B 5/1519* (2013.01); *A61B 5/1411* (2013.01); *A61B 5/150022* (2013.01);
(Continued)

(58) Field of Classification Search
CPC ................ A61B 5/1405; A61B 5/1411; A61B 5/15105–5/15113; A61B 5/15117;
(Continued)

(56) References Cited

U.S. PATENT DOCUMENTS 5,207,696 A  *  5/1993  Matwijcow ........ A61B 17/3211
                                                              30/151
5,304,193 A  *  4/1994  Zhadanov ........ A61B 5/150022
                                                              600/585
(Continued)

FOREIGN PATENT DOCUMENTS

DE      102009055874 A1    6/2011
DE      102010004370 A1    7/2011
(Continued)

OTHER PUBLICATIONS

International Search Report for PCT/US2013/059638; dated Dec. 20, 2013; 9 pgs.

*Primary Examiner* — Ryan J Severson
*Assistant Examiner* — Charles Wei
(74) *Attorney, Agent, or Firm* — Gardner Groff Greenwald & Villanueva, PC

(57) ABSTRACT

A lancing device has a charging mechanism that operates to convert an external push action by a user to an internal pull action that retracts and charges a lancet for use in a lancing stroke. In some embodiments, the charging mechanism includes a user-actuated charging push-button, a reverse charging member coupled to a lancet carrier, and a reverse-motion conversion member coupled therebetween. Depressing the user-actuated member in a first longitudinal direction causes transverse movement of the conversion member, which in turn causes longitudinal retraction of the reverse charging member and the lancet carrier coupled thereto in a second longitudinal direction opposite the first direction, thereby charging a drive mechanism of the lancing device. In other embodiments, a rack-and-pinion gear mechanism provides the same push-to-pull functionality.

17 Claims, 12 Drawing Sheets

Related U.S. Application Data

(60) Provisional application No. 61/700,634, filed on Sep. 13, 2012.

(52) U.S. Cl.
CPC ...... *A61B 5/15113* (2013.01); *A61B 5/15117* (2013.01); *A61B 5/15128* (2013.01); *A61B 5/15132* (2013.01); *A61B 5/15192* (2013.01); *A61B 5/15194* (2013.01); *A61B 5/150412* (2013.01); *A61B 5/150503* (2013.01); *A61B 5/150183* (2013.01); *A61B 5/150259* (2013.01)

(58) Field of Classification Search
CPC ............ A61B 5/15119; A61B 5/15132; A61B 5/1519; A61B 10/0045; A61B 10/0048; A61B 2010/0077; A61B 2010/008; A61B 5/15186–5/15198; A61M 5/20–2005/2093
See application file for complete search history.

(56) References Cited

U.S. PATENT DOCUMENTS

| | | | |
|---|---|---|---|
| 5,318,584 A | 6/1994 | Lange et al. | |
| 5,709,700 A * | 1/1998 | Hirota | A44C 7/001 |
| | | | 606/181 |
| 5,759,160 A | 6/1998 | Neese et al. | |
| 6,419,661 B1 | 7/2002 | Kuhr et al. | |
| 6,858,015 B2 | 2/2005 | List | |
| 6,958,072 B2 * | 10/2005 | Schraga | A61B 5/15142 |
| | | | 606/181 |
| 7,223,276 B2 | 5/2007 | List et al. | |
| 7,244,266 B2 | 7/2007 | Garthe et al. | |
| 7,273,484 B2 * | 9/2007 | Thoes | A61B 5/15186 |
| | | | 600/573 |
| 7,575,583 B1 * | 8/2009 | Schraga | A61B 5/1411 |
| | | | 606/161 |
| 7,662,111 B2 | 2/2010 | Cha et al. | |
| 7,691,117 B2 | 4/2010 | Whitson et al. | |
| 7,763,042 B2 | 7/2010 | Iio et al. | |
| 7,909,791 B2 | 3/2011 | Liniger et al. | |
| 8,092,476 B2 | 1/2012 | Curry | |
| 8,114,108 B2 | 2/2012 | Fukuzawa et al. | |
| 8,147,509 B2 | 4/2012 | Iio et al. | |
| 8,469,986 B2 * | 6/2013 | Schraga | A61B 5/1411 |
| | | | 606/182 |
| 2011/0112439 A1 | 5/2011 | Chang et al. | |
| 2011/0196261 A1 | 8/2011 | Robbins et al. | |

FOREIGN PATENT DOCUMENTS

| | | |
|---|---|---|
| EP | 1415593 A1 | 5/2004 |
| EP | 1847219 A1 | 10/2007 |

\* cited by examiner

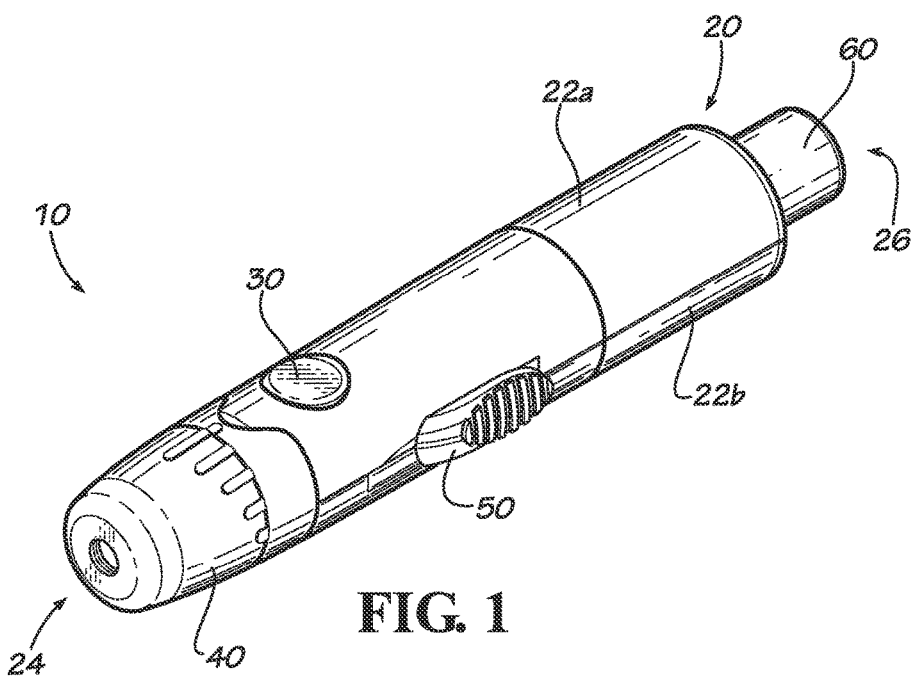
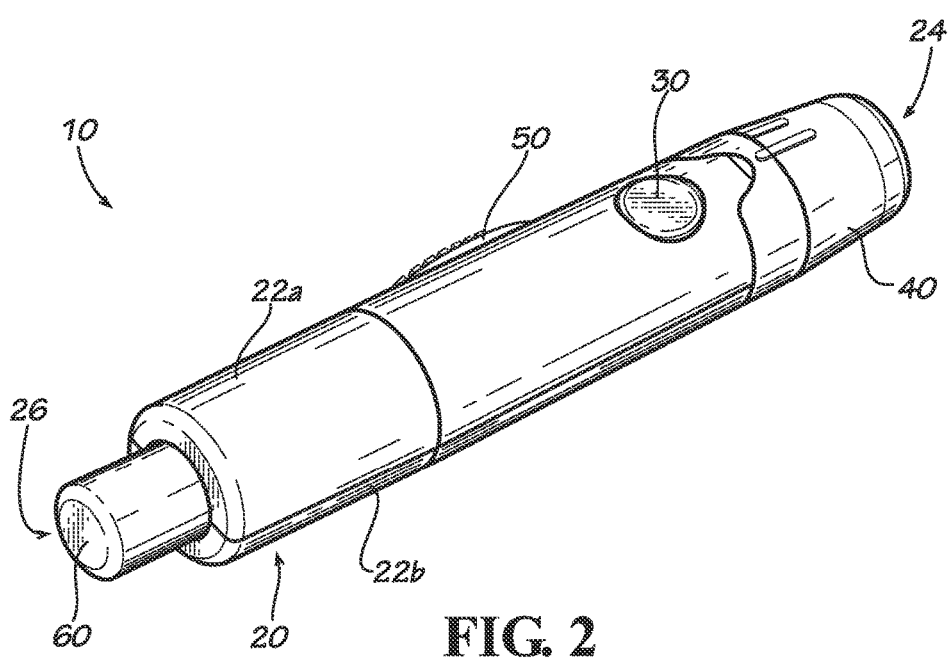

PUSH-TO-CHARGE MECHANISM FOR LANCING DEVICE

CROSS-REFERENCE TO RELATED APPLICATIONS

This application is a continuation of U.S. Non-Provisional patent application Ser. No. 14/026,129 filed Sep. 13, 2013, which claims the priority benefit of U.S. Provisional Patent Application Ser. No. 61/700,634 filed Sep. 13, 2012, the entireties of which are hereby incorporated herein by reference for all purposes.

TECHNICAL FIELD

The present invention relates generally to the field of medical devices, and more particularly to a lancing device for blood sampling and testing having an innovative charging mechanism.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. U.S. patent application Ser. No. 13/005,181 (Pub. No. US 2011/0196261) and U.S. patent application Ser. No. 12/641,674 (Pub. No. US 2010/0160942), which are incorporated herein by reference, show example lancing devices.

A lancet is typically propelled by the drive mechanism from a retracted position within the housing to an extended position wherein a sharp tip portion of the lancet projects from the housing to prick the subject's skin at a desired lancing site. Many known lancing devices use a drive mechanism that is charged or energized by pulling the drive mechanism to a retracted position. This results in the user having to perform the charging procedure by pulling the charging mechanism away from the body of the lancing device. Charging the drive mechanism by pulling the charging mechanism away from the body of the lancing device can present challenges to users with reduced manual dexterity, and may require the subject or user to use two hands to hold the device body and pull the handle until the device is charged and ready to activate.

Accordingly, it can be seen that needs exist for improved systems and methods for charging lancing devices. It is to the provision of improved lancing devices and methods of operation and use thereof that the present invention is primarily directed.

SUMMARY

In example embodiments, the present invention relates to lancing devices having an improved charging mechanism. The charging mechanism operates to convert an external push action by a user to an internal pull action that retracts and charges a lancet for use in a lancing stroke.

In one embodiment, the charging mechanism retracts and charges a lancet carrier via a cam-driven motion-conversion member with two cam surfaces. The charging mechanism includes an actuator member and a reverse charging member constrained to move only in an axial direction, and the conversion member which is movably mounted therebetween and constrained to move only in a transverse direction. Pushing actuation of the actuator member in an axial-push direction causes one of the cam surfaces to produce transverse movement of the conversion member, which in turn causes the other one of the cam surfaces to retract the reverse charging member in an axial-push direction, thereby retracting the lancet carrier coupled thereto to a charged position.

In another embodiment, the charging mechanism retracts and charges a lancet carrier via a rack-and-pinion gear mechanism that provides the same push-to-pull functionality. In this embodiment, the charging mechanism includes two rack gears engaging one pinion gear. Pushing actuation of the actuator member in an axial-push direction causes one of the rack gears to rotate the pinion gear, which in turn causes the other one of the rack gears surfaces to retract the reverse charging member in an axial-push direction, thereby retracting the lancet carrier coupled thereto to a charged position.

In another embodiment, the invention relates to a charging mechanism for inclusion in a lancing device having a drive mechanism with a lancet carrier that holds a lancet. The charging mechanism retracts and charges the lancet carrier to a charged position where it interacts with the drive mechanism for reliable retention in the charged position. The charging mechanism can be of a cam-driven or rack-and-pinion type as described herein, or of another type that converts an external push action by a user to an internal pull action that retracts and charges a lancet for use in a lancing stroke.

And in another embodiment, the invention relates to a method for charging a lancing device. The method includes slidably mounting a charging mechanism within a portion of the lancing device, movably mounting a conversion member with a portion of the charging mechanism, movably mounting a portion of the lancet carrier with the conversion member, pressing the charging mechanism into the lancing device, forcing movement of the conversion member in a direction transverse to the movement of the charging mechanism, and moving the lancet carrier in a direction generally opposite the direction of movement of the charging mechanism to charge the lancing device.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not unnecessarily restrictive of the invention, as claimed.

BRIEF DESCRIPTION OF THE DRAWINGS

FIG. 1 is a front perspective view of a lancing device according to a first example embodiment of the present invention.

FIG. 2 is a rear perspective view of the lancing device of FIG. 1.

DETAILED DESCRIPTION OF EXAMPLE

Embodiments

Figure 3:
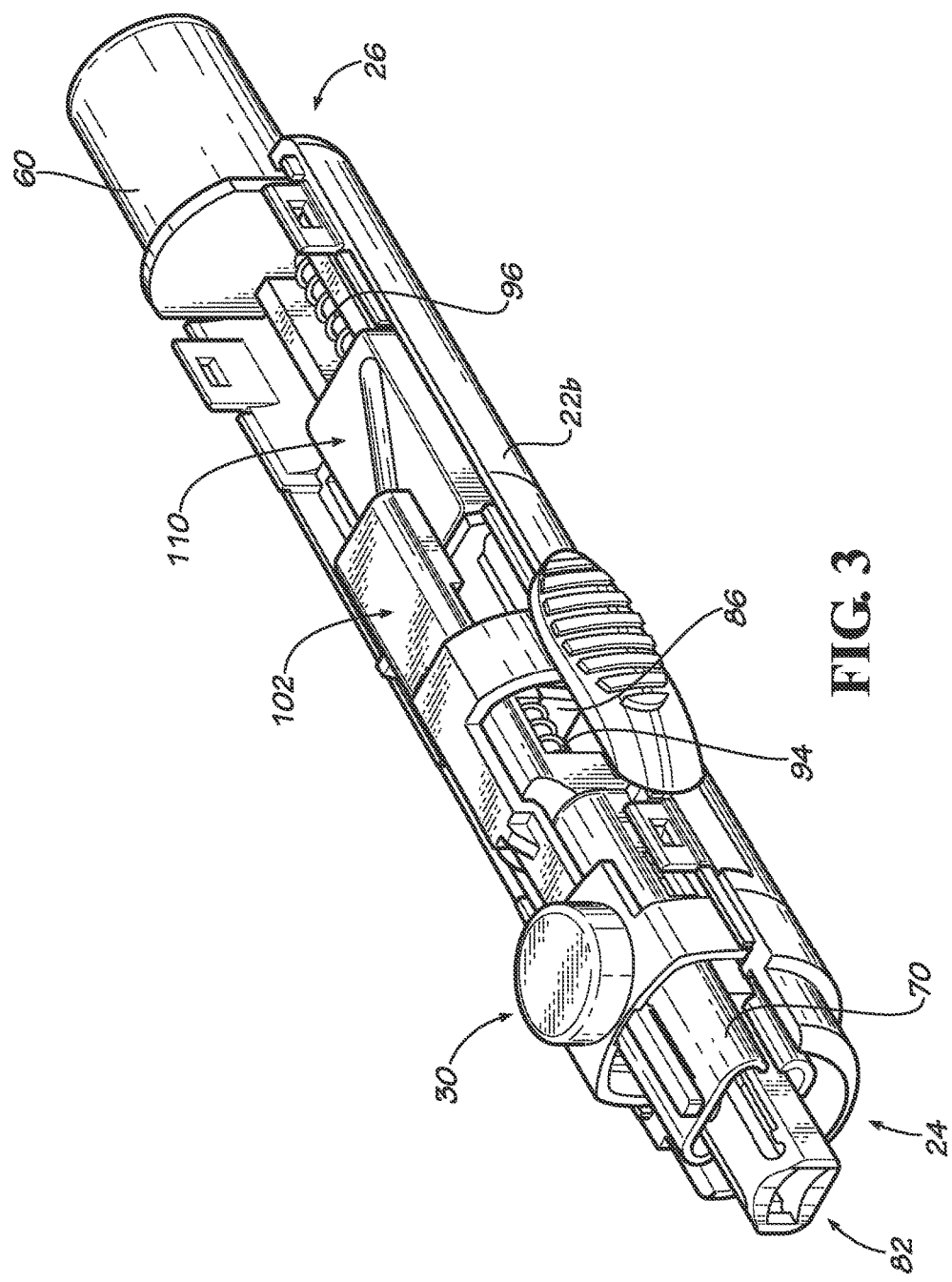
FIG. 3 shows the lancing device of FIG. 1 with portions of its housing removed to show internal components thereof.
Figure 4:
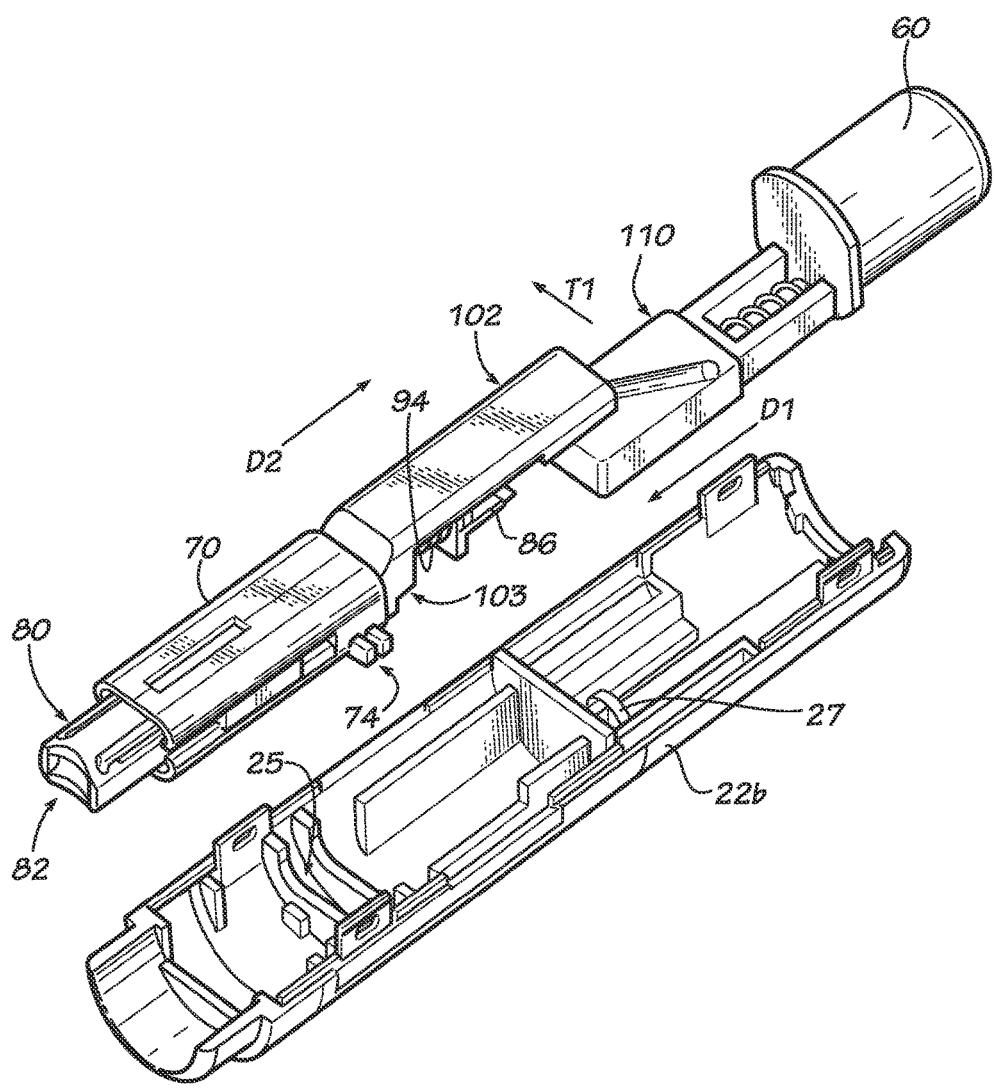
FIG. 4 is a partially-exploded view of the lancing device of FIG. 3 showing a charging mechanism.
Figure 5:
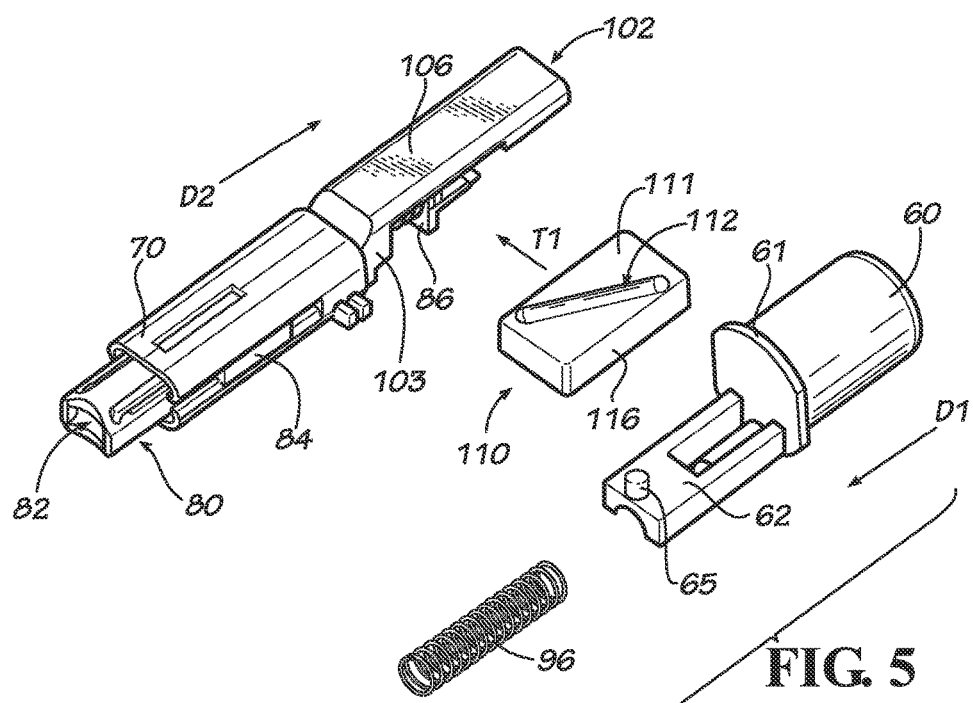
FIG. 5 is a further-exploded view of the charging mechanism of FIG. 4.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be unnecessarily limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-9D show a lancing device 10 according to a first example embodiment of the present invention. The lancing device 10 includes a charging mechanism, an actuator mechanism, a drive mechanism, and a housing 20 for these components. The drive mechanism includes a lancet carrier 80 that carries a lancet 89. The charging mechanism is operable to charge the drive mechanism, and the actuator mechanism is operable to release the lancet carrier to be driven by the charged drive mechanism to propel the lancet carrier (and thus the lancet) through a lancing stroke.

The details of the housing 20, lancet carrier 80, actuator mechanism, and drive mechanism depicted and described herein are representative and not limiting of the invention. Thus, other conventional housings, lancet carriers, actuator mechanisms, and/or drive mechanisms can be used with good results, as long as they are modified to include cooperating features that permit and do not interfere with the push-to-pull functionality provided by the charging mechanism.

Referring primarily to FIGS. 1-3, in the depicted embodiment the housing 20 is elongate and thereby defines a longitudinal axis. The housing 20 includes upper and lower housing shells 22a, 22b, and a forward or proximal end 24 defining a lancet opening through which at least a sharp tip portion of the lancet projects at the extended position of the lancing stroke to penetrate the skin of a subject. The housing 20 holds the lancet carrier 80, with the lancet carrier movably mounted in the housing for traversing the lancing stroke. In one form, the housing 20 has a lengthwise dimension in an axial direction between its forward or proximal end 24 and its rear or distal end 26 that is greater than its side-to-side width in a transverse dimension, which in turn is generally equivalent to or greater than its thickness from top to bottom. The housing can be constructed from a substantially rigid and durable material, for example a plastic or composite. In other example embodiments, the housing has other shapes and forms (e.g., disc-shaped, only one or more than two shell pieces, etc.).

Figure 8:
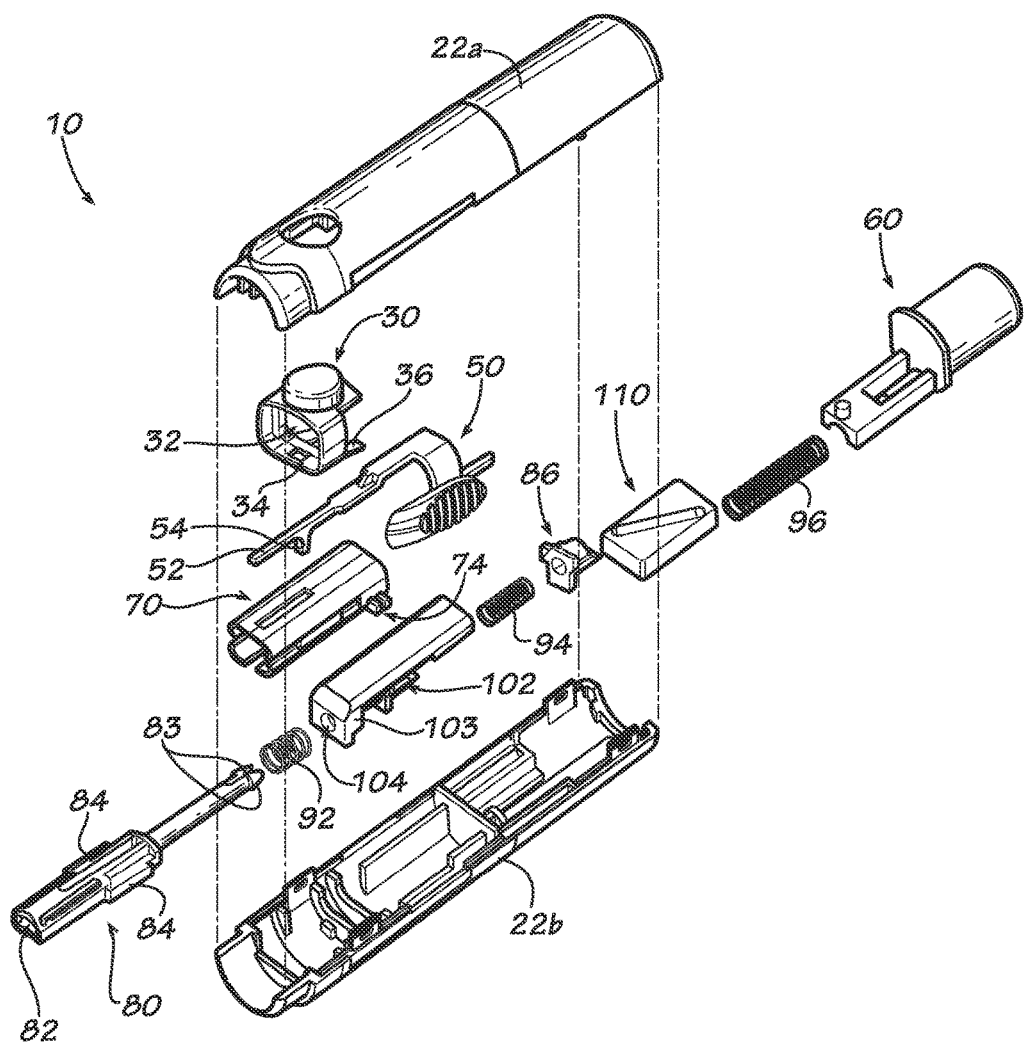
FIG. 8 is an exploded view of the lancing device of FIG. 1.

Referring primarily to FIGS. 1-2 and 8, the lancing device 10 optionally includes a removable endcap 40 and/or a lancet-ejection mechanism 50. Removal of the endcap 40 allows access for removal and replacement of the lancet 89 after use, for example by actuation of the ejection mechanism 50. Further optional, the endcap 40 can provide adjustment to the depth of penetration of the lancet tip projecting therethrough, wherein a portion of the endcap can move (e.g., rotate) relative to another portion of the endcap or housing such that the depth of penetration of the lancet tip is adjustable. In example forms, the ejection mechanism 50 movably mounts within an elongated opening along a side of the housing 20 and extends within the housing to selectively engage and eject the lancet 89 after use. For example, the ejection mechanism 50 can include an elongate finger 52 extending with a tooth 54 projecting generally transversely therefrom. The tooth 54 remains within a defined channel of the inner drive core 70 and a channel of the collar 82. The ejection mechanism 50 is actuated to force the tooth 54 against the lancet 89 within the collar 82, thereby ejecting the same therefrom. In other embodiments, a conventional endcap and/or ejection mechanism can be incorporated into the lancing device.

Referring primarily to FIGS. 3-6 and 8, details of the drive mechanism will now be described. In the depicted embodiment, the drive mechanism includes an inner drive core 70 that is engaged in a fixed position within the housing 20 by one or more inter-engaging surface features 25, 74. For example, as shown in detail in FIG. 4, the inter-engaging features can include a retaining channel 25 formed within the housing 20 and one or more tabs 74 extending from the inner drive core 70 and retained within the channel to retain the drive core in a fixed position relative to the housing. The inner drive core 70 can be provided by a separate part assembled to the housing 20, or its features can be incorporated into the housing and thus form an integral part thereof. In other embodiments, the male/female inter-engaging features are reversed/switched and/or or the inner drive core is engaged in a fixed position within the housing by other inter-engaging features such as tabs and slots, pins and holes, or other conventional fixing structures.

The drive mechanism further includes the lancet carrier 80 that carries the lancet 89. The lancet carrier 80 translationally slides within an axial bore or channel extending longitudinally through or along the inner drive core 70. In the depicted embodiment, the lancet carrier 80 has a collar or sleeve 82 at a proximal/forward end thereof for releasably engaging a lancet 89, and a distal/rear end generally opposite thereto includes resiliently flexing fingers 83 for providing engagement with a spring retainer 86 (see FIGS. 5-6). In alternative embodiments, the lancet carrier is of a conventional type. For example, in some embodiments the lancet and carrier are a single part that is replaceable (in multi-use embodiments) and/or non-replaceable (in disposable embodiments). And in other embodiments, the lancet carrier sequentially engages a series of lancets in a cartridge.

In addition, the drive mechanism further includes a drive spring 92 for propelling the lancet carrier 80 forward through an advancing portion of the lancing stroke and a return spring 94 for retracting the lancet carrier backward through a return portion of the lancing stroke. In example embodiments, the drive spring 92 and the return spring 94 are retained on the lancet carrier 80 between a medial portion of the lancet carrier defining outwardly projecting wings 84 and the spring retainer 86 coupled to the resiliently flexing fingers 83 of the lancet carrier (see FIG. 8). For example, the drive spring 92 can be retained between the distal ends of the wings 84 and a distal wall (unshown) of the inner drive core 70, and the return spring 94 can be engaged between a transverse arm 103 (see FIG. 4) of a reverse-motion charging member 102 and the spring retainer 86. In other embodiments, a single spring is provided that drives and retracts the lancet and that is mounted in place by conventional spring-constraining structures.

The lancet carrier 80 is mounted to and travels axially with the reverse charging member 102. The reverse charging member 102 can be provided by, for example, the depicted L-shaped link or another link operably connecting the lancet carrier to the charging mechanism. In the depicted embodiment, the elongate distal portion of the lancet carrier 80 extends through a bore 104 (see FIG. 8) of the transverse arm 103 of the reverse charging member 102 (see FIGS. 5-6), with the resiliently flexing fingers 83 of the elongate distal portion of the lancet carrier retaining the reverse charging member on the lancet carrier. A portion of the reverse charging member 102 engages and thus forms a portion of the charging mechanism that retracts the lancet carrier 80 upon actuation of the charging button 60, as described in more detail below. The reverse charging member 102 can be provided by a separate part assembled to the lancet carrier 80 (as depicted), or its features can be incorporated into the lancet carrier and thus form an integral part thereof. Therefore, as used herein, the reverse charging member is considered to be included as a part of the lancet carrier, so interaction of the charging mechanism with the lancet carrier broadly includes interaction with the reverse charging member.

Figure 6:
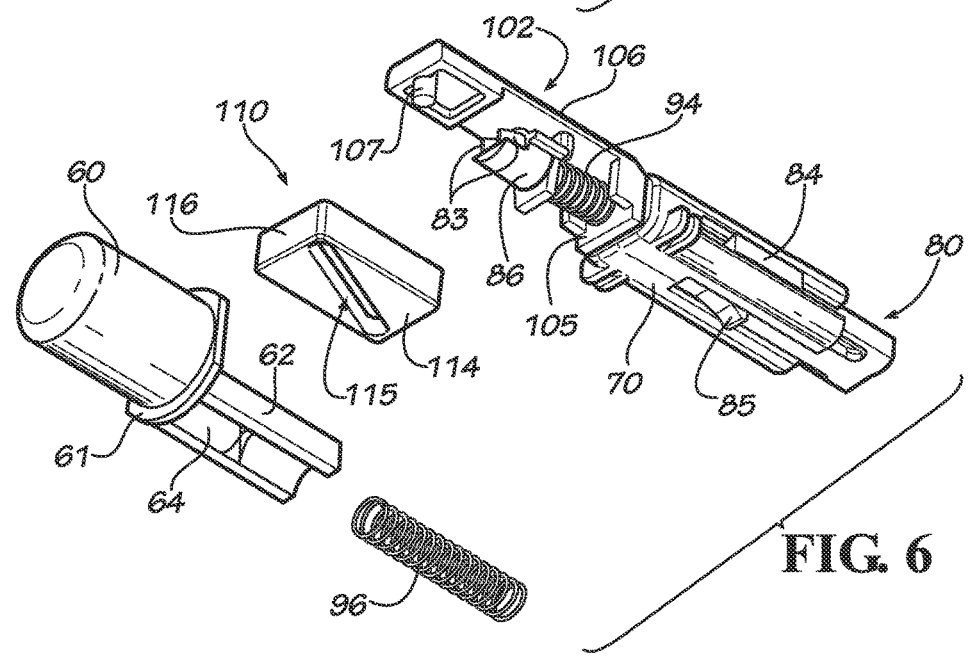
FIG. 6 is a bottom perspective exploded view of the charging mechanism of FIG. 5.

Referring primarily to FIGS. 6 and 8, the actuator mechanism is operable to actuate the lancing device 10 to propel the lancet 89 on the lancet carrier 80 through the lancing stroke from a retracted/charged position within the housing 20 to an extended/lancing position (shown in FIG. 9D) with at least a sharp tip portion 90 of the lancet projecting outwardly of the lancet opening at the proximal/forward end of the housing. The actuator mechanism includes a release actuator 30 that is activated by a user to release the lancet carrier 80 in the charged position so it can be driven by the charged drive mechanism to propel the lancet carrier through the lancing stroke.

The release actuator 30 is typically in the form of a spring-biased push-button that projects through a distal/rearward opening in the housing 20 to releasably engage a portion of the drive mechanism (see FIGS. 6, 8). The release button 30 may directly engage the lancet carrier 80 (as depicted) or indirectly engage it via another portion of the drive mechanism. The release button 30 retains the drive mechanism in the charged position when not depressed and releases the drive mechanism when depressed. In the depicted embodiment, the release button 30 is generally ring-shaped and defines a first axial bore 32 extending therethrough that receives therein the lancet carrier 80. A second lateral bore 34 is formed in a portion of the release button 30 (generally opposite the actuating portion projecting through the housing shell 22a) to provide engagement with a protrusion 85 that projects from the bottom side of the lancet carrier 80 (see FIG. 6). As such, retraction of the lancet carrier 80 causes the second lateral bore 34 to engage and retain the protrusion 85, thus retaining the lancet carrier 80 in a charged position. Additionally or alternatively, a portion of the release button 30 can include one or more resilient fingers 36 for biasing against the inner drive core 70 so that the attached thereto lancet carrier 80 is retained in the charged state when retracted and released when the release button 30 is actuated.

In other embodiments, another conventional actuator mechanism can be included. For example, in some embodiments the release actuator is in the form of a structure other than a ring-shaped push-button, for example, a spring-biased slide member or a spring-biased push-button that is L-shaped. And in other embodiments, the lancet carrier (or another portion of the drive mechanism) and the actuator mechanism include other retaining elements that cooperate to releasably retain the lancet carrier in the charged position, such as a female element on the lancet carrier and a cooperating male element on the release actuator. In other embodiments, the release actuator is configured to release/actuate the drive mechanism in another way such as by a pulling, sliding, or twisting motion. In yet other embodiments, the actuator mechanism is modified and included in the charging mechanism with modifications such that releasing the depressed charging button (described below) causes the charged lancet carrier to be released to thereby initiate the lancing stroke.

Referring primarily to FIGS. 4-8, the charging mechanism cooperates with the drive mechanism to retract the lancet carrier 80 to the charged position. The charging mechanism includes a user-actuated charging button 60, a portion of the reverse charging member 102, and a push-to-pull motion-conversion member 110 operably coupling them together. The charging button 60 and the reverse charging member 102 are constrained to travel along an axis generally parallel to (including the same as) the axis of the lancing stroke of the lancet carrier 80. For example, the housing 20 can include guidance features to transversely constrain the charging button 60 and the reverse charging member 102 but permit axial their translation. Such features include longitudinal channels slidably receiving tabs or pins, as well as other conventional axial-translation guidance features well-known in the art. The user-engaged actuating portion of the charging button 60 can be in-line with the axis of the lancing stroke (as depicted) or laterally offset from it (e.g., a transverse-extending arm). The conversion member 110 is constrained to move only laterally/transversely (i.e., along an axis generally perpendicular to the lancing stroke of the lancet carrier 80). For example, the housing 20 can include guidance features to axially constrain the conversion member 110 but permit lateral/transverse movement of it. Such features include two transverse walls of the housing that are spaced apart to receive therebetween the conversion member so that it cannot slide axially but can transversely, as well as other conventional transverse guidance features well-known in the art.

The charging button 60 is biased to a distal/rearward ready position and depressible (against the biasing force) in a proximal/forward direction by the user to the charged position. In the depicted embodiment, for example, the charging mechanism includes a charge-button spring 96 that is retained on the charging button 60 by an engagement projection 64 thereof (see FIG. 6). Preferably, the projection 64 is sized to retain a portion of the spring 96 thereon so that the spring extends therefrom and engages a stop projection 27 of the lower housing shell 22*b* (see FIG. 4). Throughout the charging procedure, the charging button 60 is biased distally rearward/outward by the spring 96 (i.e., in a direction generally opposite the first axial-push direction D1 described below). So as the charging button 60 is depressed from the distally-extended ready position to the depressed charged position to charge the drive spring 92 of the drive mechanism, the charge-button spring 96 is charged. A stop element, for example a flange or rim portion 61 of the charging button 60, contacts a portion of the housing 20 to retain the charging button on the housing and define the distally-extended ready position. As such, after performing the charging procedure to place the lancet carrier 80 in a charged state, the now-charged spring 96 returns the charging button 60 to the ready position in which the flange 61 contacts a portion of the housing 20 to retain charging button thereon (see FIG. 2). In other embodiments, the biasing effect on the charging button is provided by a leaf spring, torsion spring, or other resilient element retained in position relative to the charging button by the same or other conventional retaining structures.

The conversion member 110 is movably mounted to the charging button 60 and the reverse charging member 102 to convert an external push action on the charging button by the user to an internal pull action on the reverse charging member (and thus the lancet carrier 80). The conversion member 110 includes first and second cam surfaces that are respectively engaged by first and second cam-engaging surfaces of the reverse charging member 102 and the charging button 60 to convert a first movement of the charging button 60 in a first axial-push direction D1 to a second movement of the reverse charging member in a second/opposite axial-pull direction D2. In particular, pushing the transversely-constrained charging button 60 in the first axial direction D1 causes transverse movement T1 of the axially-constrained conversion member 110, which causes the transversely-constrained reverse charging member 102 to retract the lancet carrier 80 in the second axial direction D2. The first axial direction D1 and the second axial direction D2 are generally opposite (though not necessarily co-linear) with respect to each other.

The conversion member 110 includes a first cam surface 112 formed by (recessed in or extending from) a first side 111 thereof and a second surface 115 formed by (recessed in or extending from) a second side 114 thereof. In the depicted embodiment, first cam surface is formed by a cam slot 112 and the first cam-engaging surface is formed by a boss 107 projecting from a leg portion 106 of the reverse charging member 102 and received in the first cam slot, and the second cam surface is formed by a slot 115 and the second cam-engaging surface is formed by a boss 65 projecting from the charging button 60 and received in the second cam slot. Pushing the transversely-constrained charging button 60 in the first direction D1 axially drives the boss 65 to slide within the second cam slot 115, which causes the axially-constrained conversion member 110 to move in the transverse direction T1. As the conversion member 110 is driven in the transverse direction T1, the boss 107 of the transversely-constrained reverse charging member 102 is constrained within the first cam slot 112 and thereby axially driven in the second direction D2 to retract the lancet carrier 80 in the second direction D2. In other embodiments, the first cam-engaging surface is formed on another portion of the lancet carrier or other element of the drive mechanism, and/or the second cam-engaging surface is formed on another portion of the charging member (including another element of the charging mechanism operably coupled to the charging member).

In addition, the depicted conversion member 110 is generally box-shaped and solid, with a peripheral side 116 extending between outer edges of the first and second sides 111 and 114 and extending peripherally all the way around. In other embodiments, the conversion member is generally X-shaped, has another regular or irregular shape, and/or has a non-solid frame-like structure. For example, two cam tracks or other guidance structures, each defining a respective one of the two cam surfaces, can be assembled together or integrally formed together.

Figure 7:
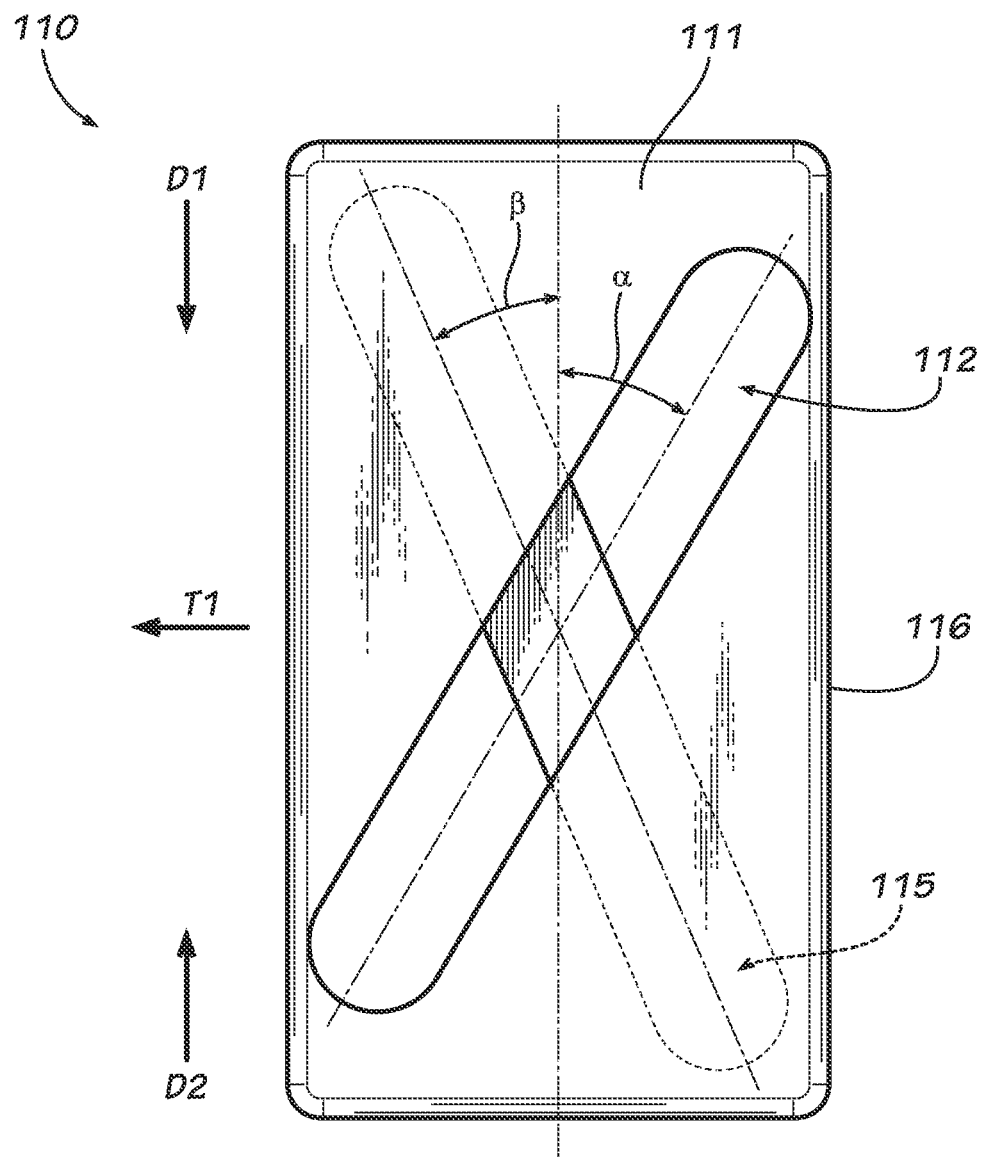
FIG. 7 is a top view of a motion-conversion member of the charging mechanism of FIG. 5.
Figure 9A:
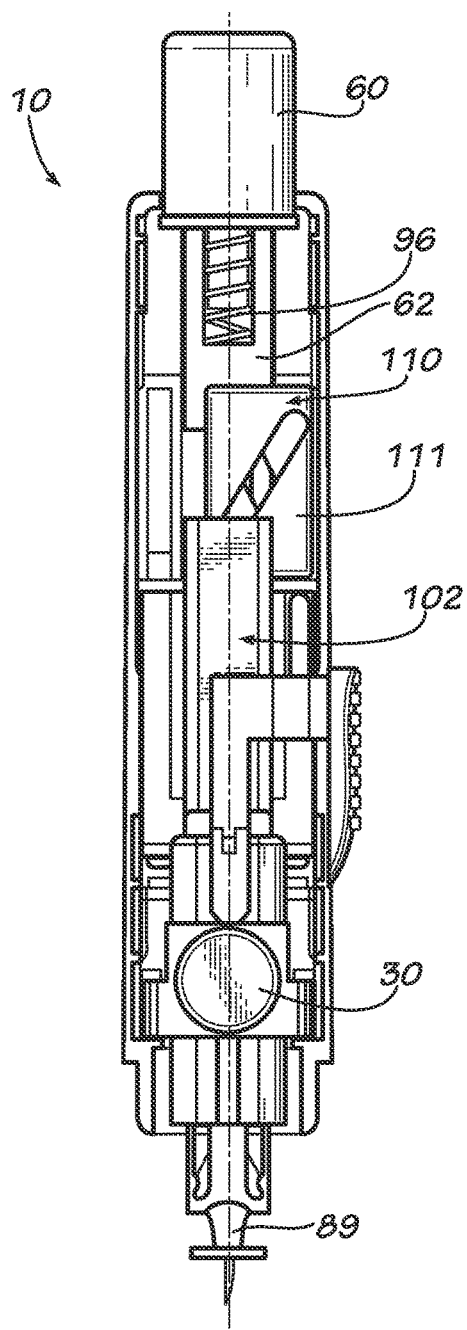
FIGS. 9A-D are top views of the lancing device of FIG. 1, with portions of its housing removed, showing the sequential operational movement of the charging mechanism between a neutral position, a charged position, a ready position, and a fully extended position of a lancing stroke.

Referring particularly to FIG. 7, the conversion member 110 will now be described in greater detail. The cam slots 112, 115 can be provided in a variety of shapes, forms, and/or configurations to provide for pulling retraction of the lancet carrier 80 by pushing actuation of the charging button 60. In the depicted embodiment, the cam slots 112, 115 are generally linear with each defining a channel in which the respective bosses 107 and 65 of the charging member 102 and the charging button 60 movably slide. Preferably, the cam slots 112, 115 are shaped smoothly with no sharp turns to provide the lancet carrier 80 with a smooth transition from the neutral state (FIG. 9A), the charging state (FIG. 9B), the charged state (FIG. 9C), the fully-extended state (FIG. 9D), and back to the neutral state (FIG. 9A). In other embodiments, the cam slots are non-linear (e.g., curved or in an undulating/sinusoidal, other regular, or irregular shape) or otherwise shaped to provide the desired push-to-pull operation of the charging mechanism. In yet other embodiments, one or both of the cam surfaces are defined by protrusions or side edges of the conversion member that are engaged by slots or ledge surfaces of the reverse charging member and/or the charging button.

In the depicted embodiment, the cam slots 112, 115 are substantially similar, but oppositely arranged from each other in a generally mirror-image fashion (e.g., at about 180 degrees from each other relative to the longitudinal axis) to form a crisscross pattern (though laterally offset from each other), such that actuation in the first axial-push direction D1 (that causes transverse movement T1 of the conversion member) forces the reverse charging member 102 to retract in the second axial-pull direction D2, thereby retracting the lancet carrier 80. In other words, the first cam slot 112 can be at an angle $\alpha$ from the longitudinal axis, and the second cam slot 115 can be at an angle $\beta$ from the longitudinal axis, with the angle $\alpha$ having generally the same (or a slightly larger) absolute value as angle $\beta$, but negative. For example, in one embodiment angle $\alpha$ is 30 degrees and angle $\beta$ is negative 23 degrees (i.e., 337 degrees).

Having described the structure of the lancing device 10, details of its operation will now be described with reference to FIGS. 9A-D. Generally described, the sequence of operation of the lancing device 10 includes the lancet carrier 80 moving from a neutral position (FIG. 9A), to a charged position (FIG. 9B), to a ready position (FIG. 9C), to a fully extended position of the lancing stroke (FIG. 9D), and back to the neutral position (FIG. 9A). In the neutral position (FIG. 9A), the conversion member 110 is positioned on one side (laterally offset from the longitudinal axis) within the housing 20, with the boss 107 of the reverse charging member 102 engaged with the first cam slot 112, and with the boss 65 of the charging button 60 engaged within the second cam slot 115. The charge-button spring 96 biases the charging button 60 distally/rearwardly to the extended position and the charging button's flange or rim 61 contacts the housing 20 to remain retained therein.

Figure 9B:
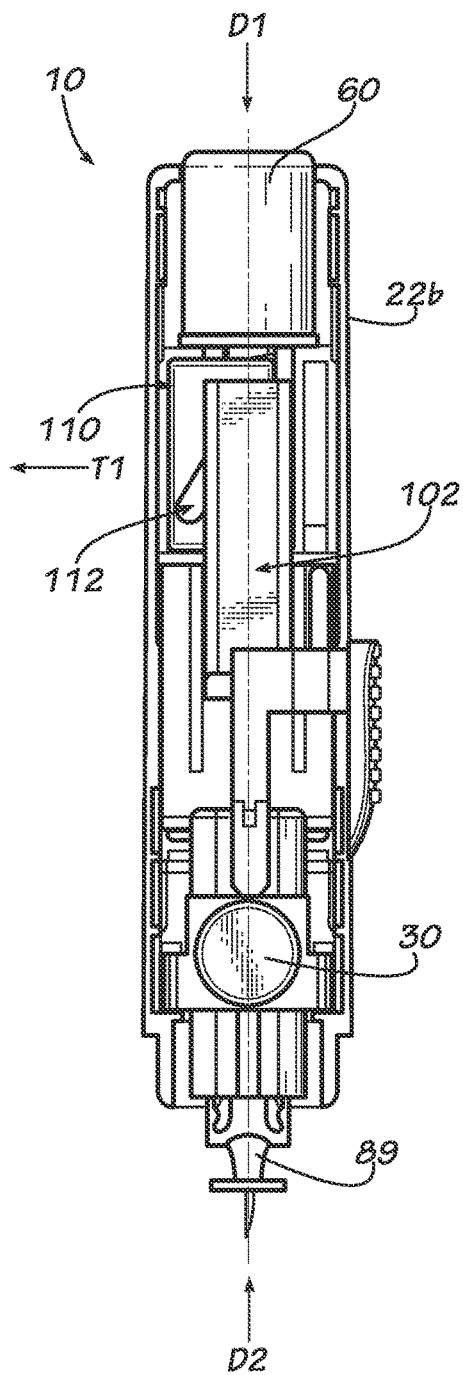

As shown in FIG. 9B, to charge the lancing device 10, the charging button 60 is pressed forward relative to the housing 20 in the first axial-push direction D1 to the depressed position, which causes the boss 65 of the charging button to move longitudinally within the angled second cam slot 115, which causes the conversion member 110 to move in the transverse direction T1. As the conversion member shifts laterally in the transverse direction T1, the angled first cam slot 112 drives the boss 107 of the reverse charging member 102 rearwardly, which causes the lancet carrier 80 to retract in the second axial-push direction D2. The retraction of the lancet carrier 80 causes the protrusion 85 extending therefrom to move into retaining engagement with the second bore 34 of the release button 30, thereby retaining the lancet carrier 80 in the charged state.

Figure 9C:
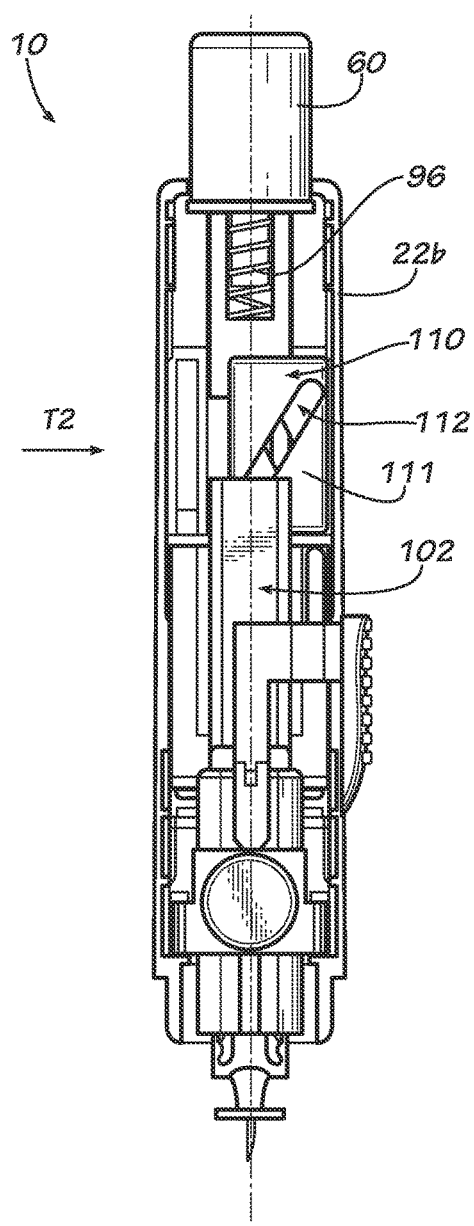
Figure 9D:
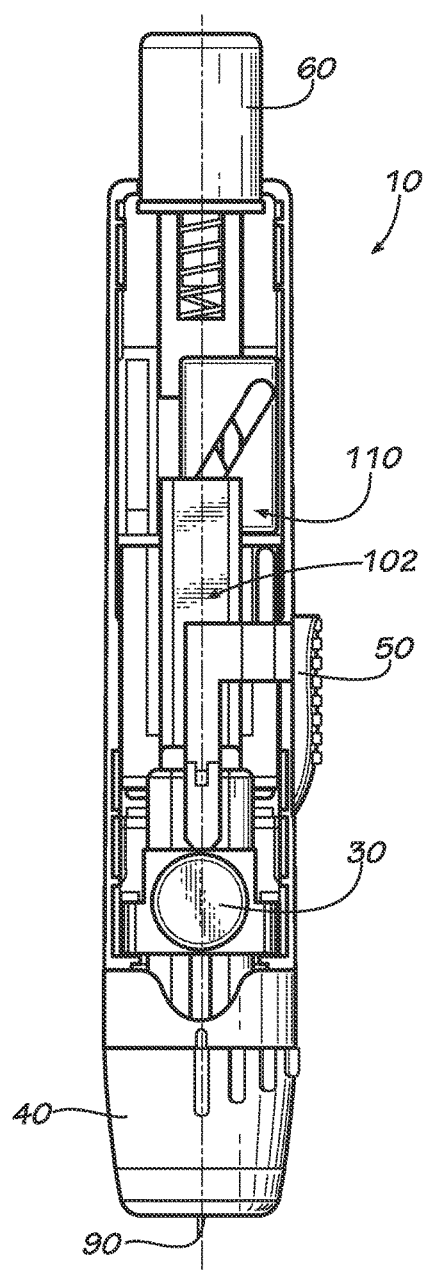
Figure 10:
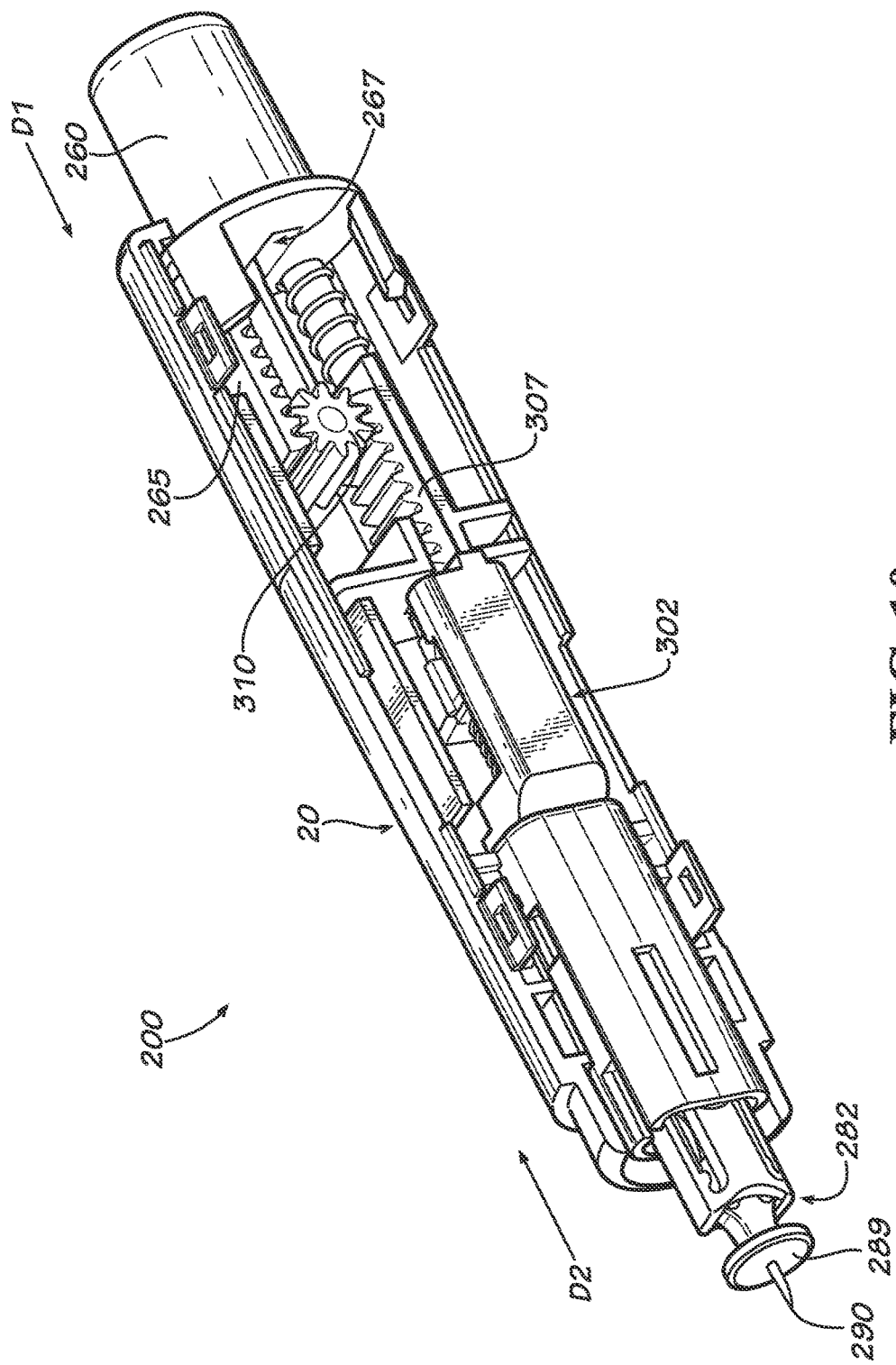
FIG. 10 is a front perspective view of a lancing device according to second example embodiment of the present invention, with portions of its external housing moved to show internal components thereof.
Figure 11:
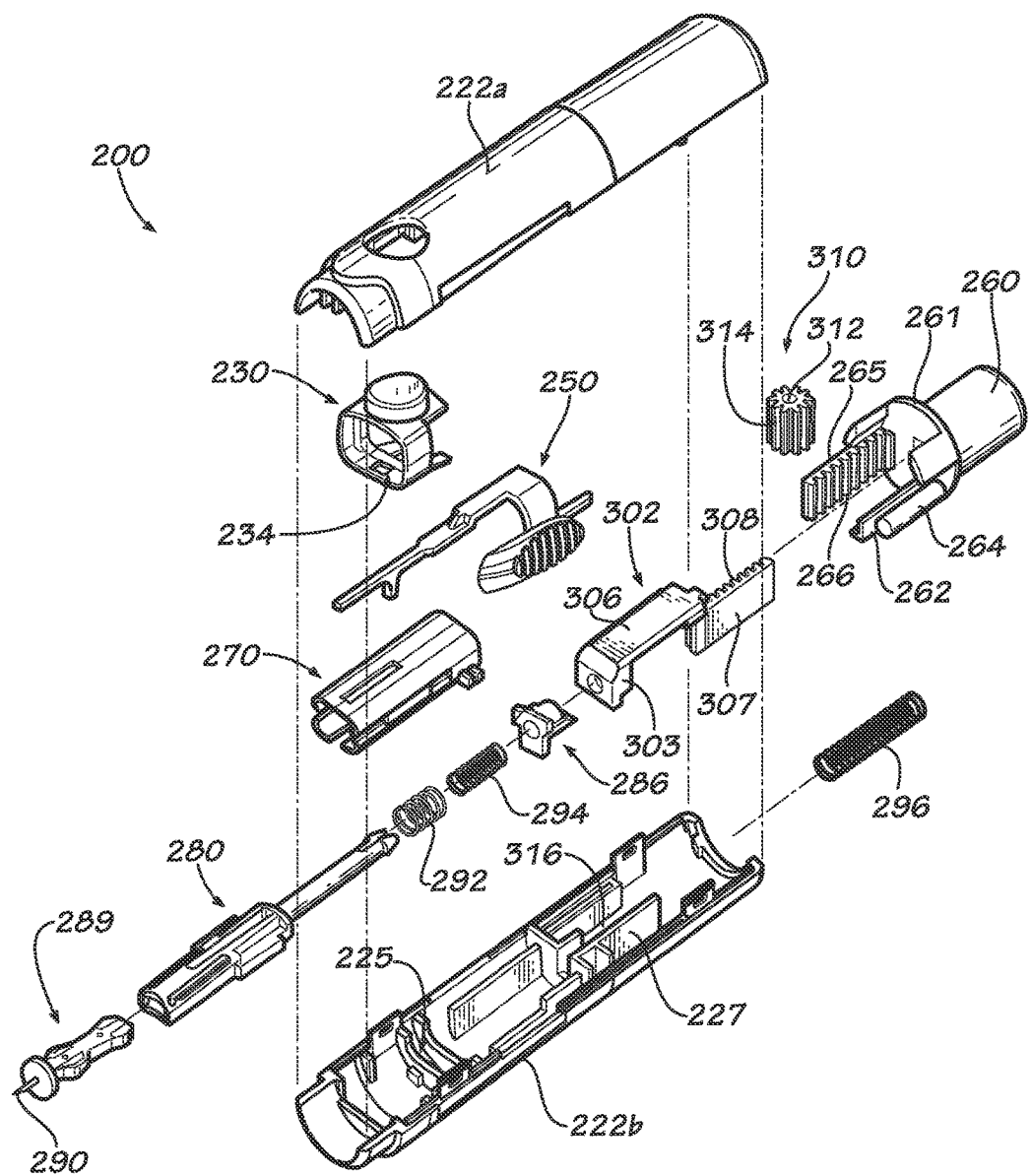
FIG. 11 is an exploded view of the lancing device of FIG. 10.

As shown in FIG. 9C, when the charging button 60 is released, the charge-button spring 96 returns the charging button to its extended position. As the charging button 60 so returns, its boss 65 drives the cam slot 115 of the conversion member 110 to cause the conversion member to move in the lateral T2 direction back to its original neutral position. The lancing device 10 is now charged and ready to be used for a lancing procedure. As shown in FIG. 9D, when the release button 30 is pressed to initiate a lancing procedure, its second bore 34 is removed from engagement with the protrusion 85 of the lancet carrier 80, thereby freeing the drive spring 92 to propel the lancet carrier along the lancing stroke to the extended position with the sharp tip portion 90 of the lancet 89 projecting out of the housing. This action charges the return spring 94, which then discharges to retract the lancet carrier 80 back to the neutral position of FIG. 9A. Optionally, removal of the endcap 40 allows for actuation of the ejection mechanism 50 to remove the used lancet 89 and replace it with a new lancet.

FIGS. 10-12D show a lancing device 200 according to a second example embodiment of the present invention. The lancing device 200 of this embodiment is substantially similar to that of the first embodiment described above. Thus, the lancing device 200 includes a charging mechanism, an actuator mechanism, a drive mechanism, and a housing for these components, with the drive mechanism including a lancet carrier that carries a lancet, and with all these components except the charging mechanism being the same or substantially similar to those of the lancing device 10 described above.

The charging mechanism of this embodiment includes a rack-and-pinion push-to-pull mechanism, rather than the cam-driven push-to-pull mechanism of the lancing device 10 of the first embodiment. Generally described, the rack-and-pinion charging mechanism includes a charging button 260 with a rack gear 265, a reverse charging member 302 (e.g., L-shaped link) with a rack gear 307, and a pinion gear 310 rotatably engaged therebetween. Pushing the charging button 260 causes the attached rack gear 265 to translate longitudinally in the first axial-push direction D1, which drives the engaged pinion gear 310 to rotate in a first angular direction (e.g., counter-clockwise), which in turn drives the reverse charging member 302 in the second opposite axial-pull direction D2. The exact configuration, size, and/or shape of the components of the rack-and-pinion charging mechanism can be selected and/or modified as desired.

The charging button 260 is generally similar to the charging button 60 of the first embodiment described above, except a noted below. In the depicted embodiment, the charging button 260 includes an elongate guide arm 262 extending longitudinally therefrom for slidably engaging a guide channel 227 (e.g., formed by the housing sidewall and a longitudinal internal wall) or other engagement feature of the lower housing shell 222b. In one form, the elongate guide arm 262 is shaped to receive guidance from the channel 227 while allowing the rack 307 to remain operative therein. The first rack 265 is formed on a portion of the charging button 260 and has a series of teeth 266 projecting therefrom. Optionally, a portion of the charging button 260 may include an orifice for allowing the rack 307 to extend therethrough when the charging button is actuated. For example, to ensure the rack 307 is fully retracted to charge the drive spring 292, an opening 267 may be provided to prevent contact between the rack 307 and the button 260.

The reverse charging member 302 is generally similar to the reverse charging member 102 as described above, except as noted below. As depicted, the second rack 307 extends from a portion of the leg portion 306 of the reverse charging member 302 in a direction generally parallel with the same, and includes a series of teeth 308 projecting in an opposite/facing direction from the teeth 266 of the first rack 265. The racks 265, 307 are configured such that the respective teeth 266, 308 projecting therefrom engage teeth 314 of the pinion 310 rotatably mounted therebetween. As described above, the charging button 260 and the reverse charging member 302 are axially constrained to traverse only along an axis generally parallel to the advancement and retraction of the lancet carrier 280.

The pinion 310 is rotatably mounted to the housing, for example by a bore 312 that receives a post 316 extending inward from the lower housing shell 222b. In example embodiments, the post 316 is laterally offset from the axis defining the advancement and retraction of the lancet carrier. The teeth 314 of the pinion 310 engage the teeth 265, 308 of the racks 265, 307 so that linear motion of the second rack produces an opposite linear motion of the first rack.

Figure 12A:
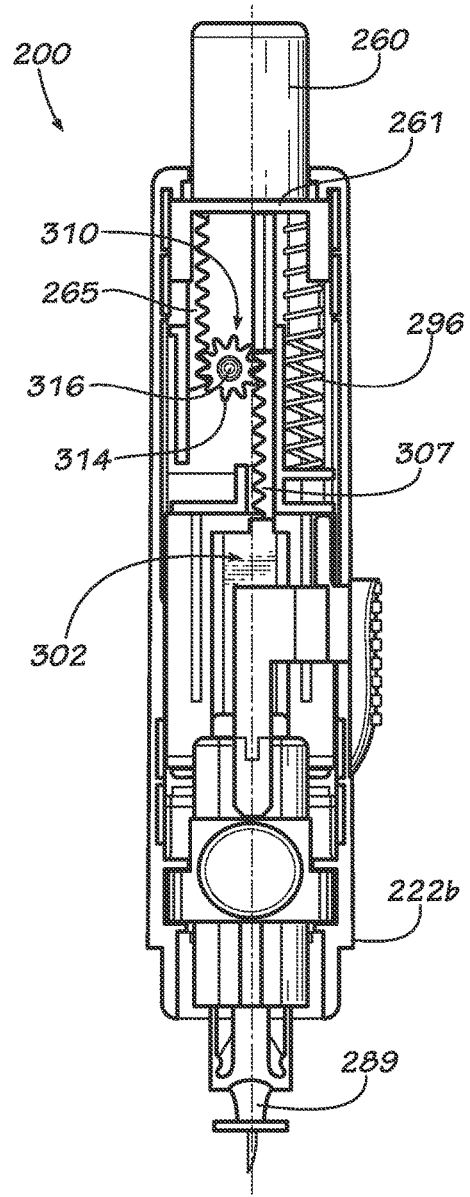
FIGS. 12A-D are top views of the lancing device of FIG. 10, with portions of its housing removed, showing the sequential operational movement of the charging mechanism between a neutral position, a charged position, a ready position, and a fully extended position of a lancing stroke.

FIGS. 12A-D show the sequential operation of the lancing device 200. The sequence of operation of the lancing device 200 generally includes the lancet carrier 280 translating from a neutral position (FIG. 12A), to a charged position (FIG. 12B), to a ready position (FIG. 12C), to a fully extended position of the lancing stroke (FIG. 12D), and back to the neutral position (FIG. 12A).

Figure 12B:
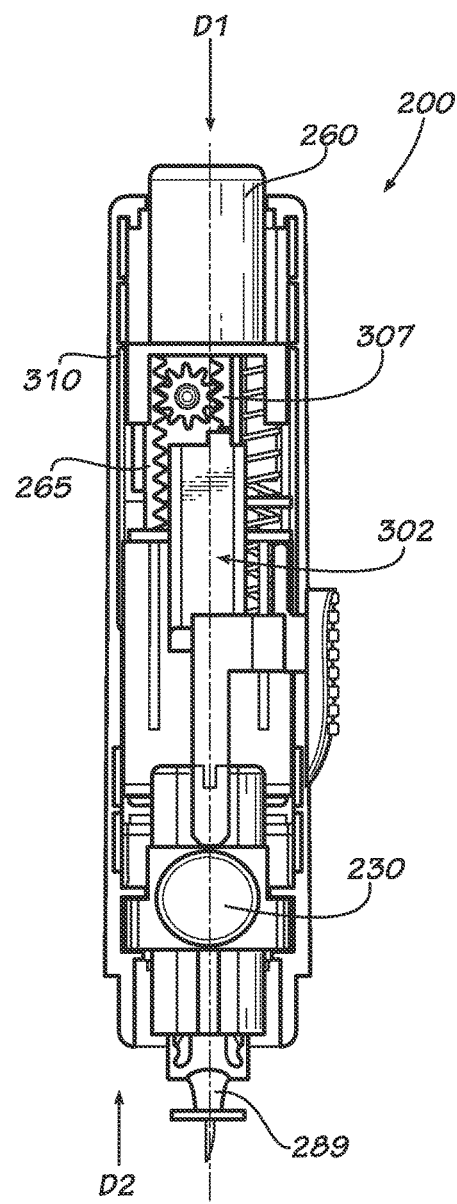

In the neutral position (FIG. 12A), the teeth 314 of the pinion 310 are engaged with both a portion of the rack 265 of the charging button 260 and with a portion of the rack 307 of the reverse charging member 302. The charge-button spring 296 biases the charging button 260 rearwardly wherein the flange or rim 261 contacts portions of the housing to remain retained therein. As best seen in FIG. 12B, the user-actuated portion of the charging button is pressed into the device 200 (first direction D1), causing the rack 265 to rotationally drive the pinion (e.g., counter-clockwise), which translationally drives and retracts the rack 307 of the reverse charging member 302 (second direction D2). As similarly described above, the release button 230 provides releasable engagement with a portion of the lancet carrier to maintain a ready position (FIG. 12C) until actuated by being pressed therein to remove the projection 285 from within the second bore 234 (see FIG. 11). After charging, the biasing spring 296 biases the charging button 260 to project outwardly wherein the flange 261 engages portions of the housing 220.

Figures 12C, 12D:
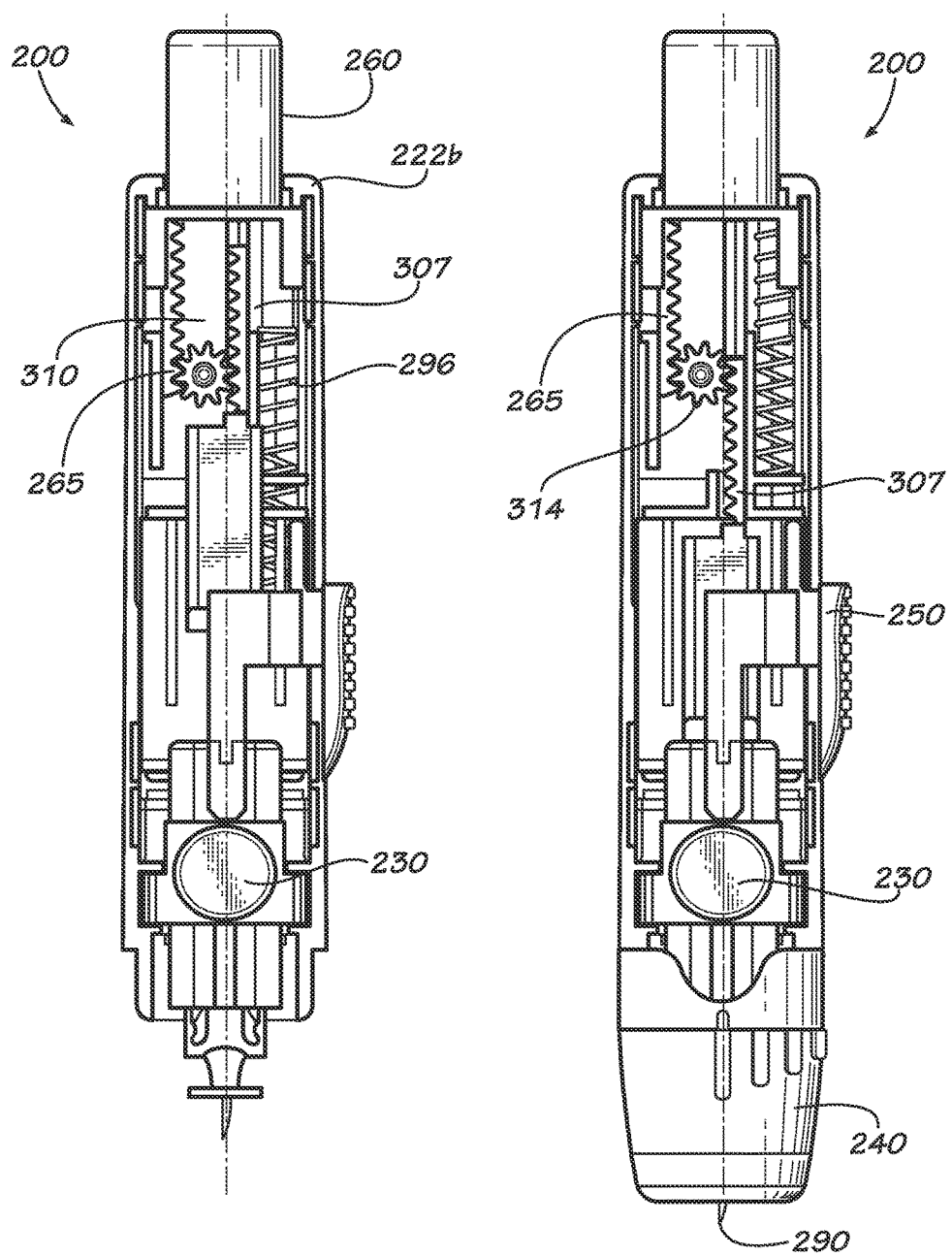

When the release button 230 is pressed, the second bore 234 of the same is removed from engagement with the protrusion 285, thereby allowing the drive spring 292 to propel the lancet carrier 80 along the lancing stroke wherein the sharp tip portion 290 of the lancet 289 projects external the housing (FIG. 12D). Preferably, the return spring 294 or other biasing members therein cause retraction of the lancet carrier back to the neutral position (FIG. 12A). Also optional, removal of the endcap 240 allows for actuation of the ejection mechanism 250 to remove the used lancet and replace with a new lancet.

In additional example embodiments, the present invention relates to a method of charging a lancing device. The method preferably comprises slidably mounting a charging mechanism within a portion of the lancing device, movably mounting a conversion member with a portion of the charging mechanism, movably mounting a portion of the lancet carrier with the conversion member, pressing the charging mechanism into the lancing device, forcing movement of the conversion member in a direction transverse to the movement of the charging mechanism, and moving the lancet carrier in a direction generally opposite the direction of movement of the charging mechanism subsequently charging the lancing device.

While the invention has been described with reference to preferred and example embodiments, it will be understood by those skilled in the art that a variety of modifications, additions and deletions are within the scope of the invention, as defined by the following claims.

What is claimed is:

1. A lancing device for propelling a lancet through a lancing stroke, the lancing device comprising:
    a housing including an axial bore;
    a drive mechanism including a lancet carrier and a drive spring, the lancet carrier holding the lancet and translatable axially within the housing through the lancing stroke, and the drive spring adapted to propel the lancet carrier through the lancing stroke; and
    a charging mechanism adapted to retract the lancet carrier to a charged position and including a charging button having a first rack gear, a reverse charging member having a second rack gear, and a pinion gear rotatably engaged between the first and second rack gears, and wherein movement of the charging button in a first axial direction causes rotation of the pinion gear, which in turn causes movement of the reverse charging member and lancet carrier coupled thereto in a second axial direction generally opposite the first axial direction to retract the lancet carrier to a charged position,
wherein the charging button includes an orifice allowing the first rack gear to extend through the housing when the charging button is actuated.

2. The lancing device of claim 1, wherein the charging button is movable between an extended position and a depressed position, and is spring-biased toward the extended position.

3. The lancing device of claim 1, wherein the housing comprises a guidance feature.

4. The lancing device of claim 3, wherein the charging button comprises an elongate guide arm extending longitudinally therefrom for slidably engaging the guidance feature.

5. The lancing device of claim 4, wherein the elongate guide arm is shaped to receive guidance from the guidance feature while allowing the second rack gear to remain operative.

6. The lancing device of claim 1, wherein the orifice is adapted to prevent contact between the charging button and the second rack gear.

7. The lancing device of claim 1, wherein the charging button and the reverse charging member are axially constrained to traverse only along an axis generally parallel to advancement and retraction of the lancet carrier.

8. The lancing device of claim 1, wherein the pinion gear is rotatably mounted to the housing by a bore that receives a post extending inward from the housing.

9. The lancing device of claim 8, wherein the post is laterally offset from an axis defining advancement and retraction of the lancet carrier.

10. A charging mechanism for a lancing device comprising a lancet carrier that carries a lancet through a lancing stroke, the charging mechanism comprising:
    a charging button slidably coupled to the lancing device to permit axial movement between an extended position and a depressed position and including a first rack gear;
    a reverse charging member coupled to the lancet carrier and including a second rack gear; and
    a pinion gear rotatably engaged between the first and second rack gears,
    wherein movement of the charging button in a first axial direction causes rotation of the pinion gear, which in turn causes movement of the reverse charging member and lancet carrier coupled thereto in a second axial direction generally opposite the first axial direction to retract the lancet carrier to a charged position;
wherein the charging mechanism is situated in a housing and wherein the housing comprises a guidance feature; and
wherein the charging button includes an orifice allowing the first rack gear to extend through the housing when the charging button is actuated.

11. The charging mechanism of claim 10, wherein the charging button is movable between an extended position and a depressed position, and is spring-biased toward the extended position.

12. The charging mechanism of claim 10, further comprising an elongate guide arm extending longitudinally therefrom for slidably engaging the guidance feature.

13. The charging mechanism of claim 12, wherein the elongate guide arm is shaped to receive guidance from the guidance feature while allowing the second rack gear to remain operative.

14. The lancing device of claim 10, wherein the orifice is adapted to prevent contact between the charging button and the second rack gear.

15. The charging mechanism of claim 10, wherein the charging button and the reverse charging member are axially constrained to traverse only along an axis generally parallel to advancement and retraction of the lancet carrier.

16. The charging mechanism of claim 10, wherein the pinion gear is rotatably mounted to the housing by a bore that receives a post extending inward from the housing.

17. The lancing device of claim 16, wherein the post is laterally offset from an axis defining advancement and retraction of the charging button.

* * * * *